United States Patent [19]

Shippey

[11] 4,397,749

[45] Aug. 9, 1983

[54] OIL-SOLUBLE METAL THIOLATE-SUCCINIMIDE COMPLEXES

[75] Inventor: Michael A. Shippey, San Rafael, Calif.

[73] Assignee: Chevron Research Company, San Francisco, Calif.

[21] Appl. No.: 344,140

[22] Filed: Jan. 29, 1982

[51] Int. Cl.³ .......................... C10M 1/38; C10M 1/54
[52] U.S. Cl. ................................ 252/42.7; 252/46.4; 252/47.5; 252/389 R; 252/400 R
[58] Field of Search .................... 252/42.7, 46.4, 47.5, 252/32.7 E, 389, 391, 400, 402; 260/429 R, 438.5 R, 439 R, 438.1

[56] References Cited

U.S. PATENT DOCUMENTS 2,553,588  5/1951  Hughes ............................. 252/46.4
3,764,534  10/1973  Blejean et al. ..................... 252/46.4

*Primary Examiner*—Jacqueline V. Howard
*Attorney, Agent, or Firm*—D. A. Newell; J. M. Whitney; V. J. Cavalieri

[57] ABSTRACT

Oil-insoluble metal thiolates prepared by reacting an acyloin, phosphorus pentasulfide and a heavy metal salt are rendered oil soluble when combined with alkenyl or alkyl mono- or bis-succinimides. The complexes are effective as anti-oxidants and anti-wear inhibitors in lubricating oils.

7 Claims, No Drawings

OIL-SOLUBLE METAL THIOLATE-SUCCINIMIDE COMPLEXES

BACKGROUND OF THE INVENTION

This invention relates to oil-soluble complexes prepared by reacting an oil-insoluble metal thiolate and an alkenyl or alkyl succinimide and the use of said complex in lubricating oils employed for crankcase lubrication of internal combustion engines.

It is well known that lubricating oils contain additives which wll enhance the oxidative stability and anti-wear properties of the oil. In view of the greater performances and useful lives required for present-day lubricating oils, more efficient and readily prepared additives are required for these purposes.

SUMMARY OF THE INVENTION

It has now been found that oil-insoluble metal thiolates may be made oil soluble and thus more effective as oil additives, by forming a complex between the metal thiolate and an alkenyl or alkyl mono- or bis-succinimide.

Thus, this invention relates to a lubricating oil composition comprising a major amount of an oil of lubricating viscosity and a minor proportion sufficient to inhibit oxidation and corrosion of a complex prepared by reacting:

(a) an alkyl or alkenyl mono- or bis-succinimide with
(b) an oil-insoluble metal thiolate prepared by reacting
(1) an acyloin of the formula:

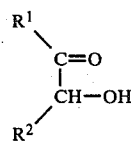

wherein $R^1$ and $R^2$ are the same or different and each is H, alkyl containing 1 to 30 carbon atoms, aryl containing 6 to 10 carbon atoms, alkaryl containing 7 to 30 carbon atoms, aralkyl containing 7 to 30 carbon atoms, or together $R^1$ and $R^2$ are alkylene and form a cyclic ring containing 4 to 6 carbon atoms which includes the carbon atoms to which they are attached, with phosphorus pentasulfide in an inert solvent at a temperature of from 25° C. to 180° C.;

wherein the mole ratio of acyloin to phosphorus pentasulfide is at least 1 to 2; and (2) reacting the product from (1) with an aqeuous solution of a reactive water-soluble, ionizable compound of a heavy metal where the final product has a thiolato ligend of the formula:

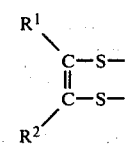

to metal ratio of from 0.5:1 to 1.5:1; and
wherein the weight ratio of (a) to (b) is in the range of from 2:1 to 10:1.

DETAILED DESCRIPTION

The metal thiolates used to prepare the oil-soluble succinimide complexes are prepared by (a) reacting an acyloin of the formula:

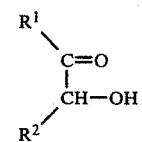

wherein $R^1$ and $R^2$ are described above with phosphorus pentasulfide in an inert solvent at a temperature of from 25° C. to 180° C.; and (b) reacting the product from (a) with an aqueous solution of a reactive water-soluble, ionizable compound of a metal whose thioorganic complex is desired.

The mole ratio of acyloin to phosphorus pentasulfide is at least 1 to 2 and may be as high as 1 to 5 and greater. A 1 to 2 mole ratio of acyloin to phosphorus pentasulfide is preferred.

Temperatures in the range of 25° C. to 180° C. may be used and preferably in the range of the reflux temperature of the particular solvent being used.

Suitable inert organic solvents which can be employed in the reaction include dioxane, toluene, xylene, the dimethyl ethers of ethylene and diethylene glycol, tetrahydrothiophene, sulfolane, carbon disulfide, and the like.

Generally, an acyloin, such as benzoin, is reacted with phosphorus pentasulfide in a solvent such as toluene, at an elevated temperature, preferably the reflux temperature of the solvent. The resulting solution is then contacted with a salt of the metal whose thioorganic complex is desired.

The exact structure of the metal thiolates is not known for certain; however, chemical analysis of the products indicate that the final product has a dithiolato ligend of the formula:

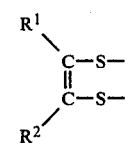

wherein $R^1$ and $R^2$ are defined above, to metal ratio of from 0.5 to 1 to 1.5 to 1.

For example, while not intending to be limited to any particular structure, it is believed that the predominant species prepared in the case of the molybdenum thiolates have the structural formula:

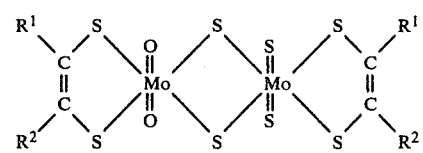

wherein $R^1$ and $R^2$ are as defined above.

It has also been found that the metal thiolates thus prepared are essentially insoluble in lubricating oils and as such have little or no utility when used alone as an additive for lubricating oils. It is only when the metal thiolates prepared as described above are complexed with an oil-soluble alkenyl or alkyl mono- or bis-succinimide that they become oil soluble and effective anti-oxidants and anti-wear additives for lubricating oils.

The heavy metals which are useful in this invention are water-soluble, ionizable compounds. Preferably, the metals are selected from Groups I-B, II-B, IV-B, V-B, VI-B, VII-B, and VIII of the periodic classification of elements.

The most preferred metals which are useful in this invention include those metals selected from the group consisting of cobalt, chromium, copper, tungsten, nickel, iron, titanium, vanadium, and molybdenum.

The metal salts which are useful include the water-soluble, ionizable compounds and include sulfates, nitrates, halides such as chlorides, carbonates, and the like. Examples of the metal salts include $FeSO_4$, $Na_2WO_4$, $VCl_3$, $NiCl_2$, $Na_2MoO_4$, $TiCl_4$, $CuCl_2$, $Na_2CrO_4$, and $CoCl_2$.

The metal salts are present in the reaction mixture in an amount sufficient to provide from 1 to 2 equivalents of metal per mole of acyloin and preferably 1 equivalent of metal per mole of acyloin.

Representative of the alkyl groups containing 1 to 30 carbon atoms in the definition of $R^1$ and $R^2$ include straight-chain, branch-chain, primary, secondary, and tertiary alkyl groups. Examples of suitable groups are methyl, ethyl, isopropyl, octyl, dodecyl, octadecyl, n-eicosyl, n-tricontyl, and the like. The preferred alkyl group contains from 1 to 20 carbon atoms.

Representative of the aryl groups containing 6 to 10 carbon atoms in the definition of $R^1$ and $R^2$ include phenyl and naphthyl, and preferably phenyl. Optionally, the aryl groups may be substituted by one or more halogens such as chloro or bromo.

Representative of the alkaryl groups containing 7 to 30 carbon atoms include methylphenyl, ethylphenyl, butylphenyl, and butylnaphthyl. Preferably, the alkaryl groups contain from 7 to 20 carbon atoms.

Representative of the aralkyl groups containing from 7 to 30 carbon atoms include benzyl, phenylethyl, and the like. Preferably, the aralkyl group contains from 7 to 20 carbon atoms.

The oil-soluble alkenyl or alkyl mono- or bis-succinimides which are employed in the additive combination of this invention are generally known as lubricating oil dispersants and are described in U.S. Pat. Nos. 2,992,708; 3,018,291; 3,024,237; 3,100,673; 3,219,666; 3,172,892; and 3,272,746; the disclosures of which are incorporated herein by reference. The preferred alkenyl or alkyl mono- or bis-succinimides are those of the formula:

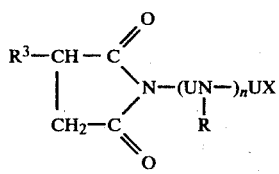

wherein X is

where R is hydrogen or alkyl of 1 to 5 carbon atoms or a group of the formula:

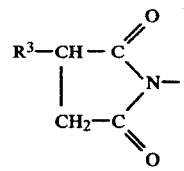

wherein $R^3$ is an alkyl or alkenyl group containing from about 20 to 300 carbon atoms; U is alkylene containing 1 to 8 carbon atoms; and n is an integer of from 1 to 9.

The preferred materials are prepared by reacting an alkenyl- or alkyl-substituted succinic anhydride of the formula:

$$R^3-CH-C\overset{\displaystyle O}{\underset{\displaystyle O}{\diagdown}}$$
$$|\qquad\qquad O$$
$$CH_2-C\overset{\displaystyle \diagup}{\underset{\displaystyle \diagdown O}{}}$$

wherein $R^3$ is defined above, with a polyalkylene-polyamine of the formula:

$$H_2N\!+\!UN\!-\!)_n\!-\!UN\!-\!H$$
$$\qquad\quad |\qquad\quad |$$
$$\qquad\quad R\qquad\quad R$$

wherein n is an integer of from 1 to about 9, preferably 1 to 4 and most preferably 3 or 4, r is hydrogen or a lower alkyl hydrocarbon substituent containing up to 5 carbon atoms and U is a lower alkylene, i.e., divalent, open chain, hydrocarbon group having from 1 to 8 carbon atoms, preferably 2 to 6 carbon atoms and most preferably 2 to 3 carbon atoms. Such polyalkylene amines include methylene amines, ethylene amines, propylene amines, butylene amines, pentylene amines, hexylene amines, heptylene amines, octylene amines, and other polymethylene amines which contain from 2 to 10 alkylene groups and 3 to 11 nitrogens. Specific examples of such polyalkylene amines include dimethylene triamine, trimethylene tetramine, tetramethylpentamine, pentaethylene hexamine, heptaethylene octamine, dipropylene triamine, tripropylene tetramine, tetrapropylene pentamine, dibutylene triamine, tributylene tetramine, tetrabutylene pentamine, dimethyl triamine, trimethylene tetramine, tetramethylene pentamine, pentamethylene hexamine, di(heptamethylene) triamine, di(trimethylene) triamine, decaethylene hendecamine, decamethylene hendecamine, $N_1,N_3$-dimethyl diethylene triamine, $N_1,N_5$-dimethyl tetraethylene pentamine, $N_1,N_5$-diethyl tetraethylene pentamine, dipentylene triamine, trihexylene tetramine, tetraheptylene pentamine, trioctylene tetramine, and tetrapentylene pentamine among others.

Also, the cyclic and higher homologes of such amines such as amino-alkyl-substituted piperazines and imidazolines as well as hydroxyalkyl-substituted alkylene amines, i.e., alkylene amines having one or more hydroxyalkyl substituents on the nitrogen atoms, are likewise contemplated for use herein.

The preferred alkylene group designated by U contains from 2 to 6 carbon atoms. Illustrative preferred alkylene groups are ethylene, propylene, 1,2-propylene, tetramethylene, and hexamethylene. The most preferred alkylene groups are from 2 to 3 carbon atoms, there being 2 carbon atoms between the nitrogen atoms.

Preferred examples of suitable amine compounds include: 1,2-diaminoethane; 1,3-diaminopropane; 1,4-diaminobutane; 1,6-diaminohexane; diethylene triamine; triethylene tetramine; tetraethylene pentamine; 1,2-propylene diamine; and the like.

A product comprising predominantly mono- or bis-succinimide can be prepared by controlling the molar ratios of the reactants. Thus, for example, if one mole of amine is reacted with one mole of the alkenyl- or alkyl-substituted succinic anhydride, a predominantly mono-succinimide product will be prepared. If two moles of the succinic anhydride are reacted per mole of polyamine, a bis-succinimide will be prepared.

The preparation of the alkenyl-substituted succinic anhydride by reaction with a polyolefin and maleic anhydride has been described, e.g., U.S. Pat. Nos. 3,018,250 and 3,024,195. Reduction of the alkenyl-substituted succinic anhydride yields the corresponding alkyl derivative. Polyolefin polymers for reaction with the maleic anhydride are polymers comprising a major amount of $C_2$ to $C_5$ mono-olefin, e.g., ethylene, propylene, butylene, isobutylene and pentene. The polymers can be homopolymers such as polyisobutylene as well as copolymers of two or more such olefins such as copolymers of: ethylene and propylene; butylene and isobutylene; etc. Other copolymers include those in which a minor amount of the copolymer monomers, e.g., 1 to 20 mole %, is a $C_4$ to $C_8$ nonconjugated diolefin, e.g., a copolymer of isobutylene and butadiene or a copolymer of ethylene, propylene and 1,4-hexadiene, etc.

The olefin polymers contain from about 20 to 300 carbon atoms and preferably from 30 to 150 carbon atoms. An especially preferred polyolefin is polyisobutylene.

Another embodiment of this invention involves the preparation of oil-soluble metal thiolate-succinate complexes.

Oil-soluble alkenyl or alkyl mono- or bis-succinates may be used in combination with or in place of the succinimides in equivalent amounts in preparing the oil-soluble metal thiolate complexes. The preparation of alkenyl succinates has also been described in the art. See for example, U.S. Pat. Nos. 3,381,022 and 3,522,179, the disclosures of which are incorporated by reference. Reduction of the alkenyl group by methods known in the art yields the corresponding alkyl succinates.

The alkenyl succinates are those of the above-described succinic anhydride with hydroxy compounds which may be aliphatic compounds such as monohydric and polyhydric alcohols or aromatic compounds such as phenols and naphthols. The aromatic hydroxy compounds from which the esters may be derived are illustrated by the following specific examples: phenol, beta-naphthol, alpha-naphthol, cresol, resorcinol, catehol, p,p'-dihydroxybiphenyl, 2-chlorophenol, 2,4-dibutylphenol, propene tetramer-substituted phenol, didodecylphenol, 4,4'-methylene-bis-phenol, alpha-decyl-beta-naphthol, polyisobutene(molecular weight of 1000)-substituted phenol, the condensation product of heptylphenol with 0.5 mole of formaldehyde, the condensation product of octylphenol with acetone, di(hydroxyphenyl)oxide, di-(hydroxyphenyl)sulfide, di(hydroxyphenyl)disulfide, and 4-cyclohexylphenol. Phenol and alkylated phenols having up to three alkyl substituents are preferred. Each of the alkyl substituents may contain 100 or more carbon atoms.

The alcohols from which the esters may be derived preferably contain up to about 40 aliphatic carbon atoms. They may be monohydric alcohols such as methanol, ethanol, isooctanol, dodecanol, cyclohexanol, cyclopentanol, behenyl alcohol, hexatriacontanol, neopentyl alcohol, isobutyl alcohol, benzyl alcohol, beta-phenylethyl alcohol, 2-methylcyclohexanol, beta-chloroethanol, monomethyl ether of ethylene glycol, monobutyl ether of ethylene glycol, monopropyl ether of diethylene glycol, monododecyl ether of triethylene glycol, monooleate of ethylene glycol, monostearate of diethylene glycol, sec-pentyl alcohol, tert-butyl alcohol, 5-bromo-dodecanol, nitro-octadecanol and dioleate of glycerol. The polyhydric alcohols preferably contain from 2 to about 10 hydroxy radicals. They are illustrated by, for example, ethylene glycol, diethylene glycol, triethylene glycol, tetraethylene glycol, dipropylene glycol, tripropylene glycol, dibutylene glycol, tributylene glycol, and other alkylene glycols in which the alkylene radical contains from 2 to about 8 carbon atoms. Other useful polyhydric alcohols include glycerol, monooleate of glycerol, monomethyl ether of glycerol, pentraerythritol, 9,10-dihydroxy stearic acid, methyl ester of 9,10-dihydroxy stearic acid, 1,2-butanediol, 2,3-hexanediol, 2,4-hexanediol, pinacol, erythritol, arabitol, sorbitol, mannitol, 1,2-cyclohexanediol, and xylene glycol. Carbohydrates such as sugars, starches, celluloses, etc., likewise may yield esters. The carbohydrates may be exemplified by a glucose, fructose, sucrose, rhamnose, mannose, glyceraldehyde, and galactose.

An especially preferred class of polyhydric alcohols are those having at least three hydroxy radicals, some of which have been esterified with a monocarboxylic acid having from about 8 to about 30 carbon atoms such as octanoic acid, oleic acid, stearic acid, linoleic acid, dodecanoic acid, or tall oil acid. Examples of such partially esterified polyhydric alcohols are the monooleate of sorbitol, distearate of sorbitol, monooleate of glycerol, monostearate of glycerol, di-dodecanoate of erythritol.

The esters may also be derived from unsaturated alcohols such as allyl alcohol, cinnamyl alcohol, propargyl alcohol, 1-cyclohexene-3-ol, an oleyl alcohol. Still other classes of the alcohols capable of yielding the esters of this invention comprises the ether-alcohols and amino-alcohols including, for example, the oxyalkylene-, oxy-arylene-, amino-alkylene-, and amino-arylene-substituted alcohols having one or more oxy-alkylene, amino-alkylene or amino-arylene oxy-arylene radicals. They are exemplified by Cellosolve, carbitol, phenoxyethanol, heptylphenyl-(oxypropylene)$_6$-H, octyl(oxyethylene)$_{30}$-H, phenyl(oxyoctylene)$_2$-H, mono(heptylphenyl-oxypropylene)-substituted glycerol, poly(styrene oxide), amino-ethanol, 3-amino ethyl-pentanol, di(hydroxyethyl)amine, p-aminophenol, tri(hydroxypropyl)amine, N-hydroxyethyl ethylene diamine, N,N,N',N'-tetrahydroxytrimethylene diamine, and the like. For the most part, the ether-alcohols having up to about 150 oxy-alkylene radicals in which the alkylene radical contains from 1 to about 8 carbon atoms are preferred.

The esters may be di-esters of succinic acids or acidic esters, i.e., partially esterified succinic acids, as well as partially esterified polyhydric alcohols or phenols, i.e., esters having free alcoholic or phenolic hydroxyl radicals. Mixtures of the above-illustrated esters likewise are contemplated within the scope of the invention.

The lubricating oils of this invention contain an oil of lubricating viscosity and a complex which provides from about 1 to 30 mmoles/kg and preferably from 2 to 18 mmoles/kg of the oil-insoluble metal thiolate and from 1.5 to 15 weight percent and preferably from 3 to 8 weight percent of the alkenyl or alkyl succinimide.

The complex, the exact structure of which is not known, may be formed by reacting the metal thiolate and the succinimide together neat at a temperature above the melting point of the mixture of reactants and below the decomposition temperature, or in a diluent in which both reactants are soluble. For example, the reactants may be combined in the proper ratio and heated together to form a homogeneous product which may be added to the oil or the reactants may be combined in the proper ratio in a solvent such as toluene, dioxane or tetrahydrofuran, the solvent stripped off, and the complex thus formed may be added to the oil.

The diluent is preferably inert to the reactants and products formed and is used in an amount sufficient to insure solubility of the reactants and to enable the mixture to be efficiently stirred.

Temperatures for preparing the complex may be in the range of from 25° C. to 180° C. and preferably 60° to 145° C. depending on whether the complex is prepared neat or in a diluent, i.e., lower temperatures may be used when a solvent is used. Since the metal thiolates are essentially insoluble in oil, the complex may not be made in-situ in the oil, e.g., addition of the insoluble metal thiolate to an oil containing the appropriate ratio of a succinimide does not solubilize the metal thiolate.

Weight percent ratios of alkenyl or alkyl mono- or bis-succinimides to metal thiolate in the complex in the range of 2:1 to 10:1 and preferably from 4:1 to 5:1 should be maintained. Lesser amounts of the succinimide will result in precipitation of the metal thiolate.

Additive concentrates are also included within the scope of this invention. They usually include from about 90 to 10 weight percent of an oil of lubricating viscosity and are normally formulated to have about 10 times the additive concentration that would be used in the finished lubricating oil composition. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although any oil of lubricating viscosity can be used.

Suitable lubricating oils which can be used to prepare a lubricating oil composition or concentrate are oils of lubricating viscosity derived from petroleum or synthetic sources. The oils can be paraffinic, naphthenic, halo-substituted hydrocarbons, synthetic esters, hydrocarbon synthetic oils, or combinations thereof. Oils of lubricating viscosity have viscosities in the range from 35 to 50,000 SUS at 100° F., and more usually from about 50 to 10,000 SUS at 100° F.

Useful synthetic hydrocarbon oils include liquid polymers of alpha-olefins having the proper viscosity. Especially useful are the hydrogenated liquid oligomers of $C_{6-12}$ alpha-olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate, and the like. Complex esters prepared from mixtures of mono- and di-carboxylic acid and mono- and di-hydroxy alkanols can also be used.

Other conventional additives which can be used in combinations with the additive combination of this invention include oxidation inhibitors, anti-foam agents, viscosity index improvers, pour-point depressants, and the like. These include such compositions as chlorinated wax, benzyl disulfide, sulfurized sperm oils, sulfurized terpene, phosphorus esters such as trihydrocarbon phosphites, metal thiocarbamates such as zinc dioctyldithiocarbamate, polyisobutylene having an average molecular weight of 100,000, etc.

The lubricating oil compositions of the invention are useful for lubricating internal combustion engines, automatic transmissions and as industrial oils such as hydraulic oils, heat-transfer oils, torque fluids, etc.

The following examples are presented to illustrate the operation of the invention and are not intended to be a limitation upon the scope of the claims.

EXAMPLES

Example 1

Preparation of Metal Thiolates

A 5-liter, 3-necked flask equipped with a stirrer, condensor and an NaOH trap was charged with 50 gm (0.235 mole) of benzoin and 500 ml of dioxane. To this mixture was added 104.7 gm (0.470 mole) $P_2S_5$ and 30.5 gm (0.229 mole) of $(NH_4)_2SO_4$ and the reaction mixture was heated at reflux for 3 hours. After cooling to about 25° C., the reaction mixture was filtered and the filter cake was washed with about 100 ml dioxane. The filtrate was transferred to a second 5-liter flask equipped with a stirrer, condensor and trap. To this filtrate was added an aqueous solution containing 40 gm (0.167 mole) $NaMoO_4.H_2O$ in about 100 ml of water. After refluxing for about 2 hours, the reaction mixture was cooled and filtered. The product was washed thoroughly with an aqueous solution of saturated $Na_2S$ and dried in a vacuum oven. Found: Mo, 17.2% (neutron activation); C, 36%; S, 45.0%; P, >1%.

In a similar fashion, each of the metal Fe, V, W, Ni, Cu, Co, Cr and Ti thiolate complexes were prepared by substituting an equivalent amount of the respective metal salt such as $FeSO_4$, $VCl_3$, $Na_2WO_4$, $NiCl_2$, $CuCl_2$, $CoCl_2$, $Na_2CrO_2$ and $TiCl_4$ in place of the $Na_2MoO_4.H_2O$ in the above procedure.

Example 2

Various metal thiolate-succinimide complexes of this invention were prepared and are reported in Table 1.

Each of the metal thiolate-succinimide complexes were prepared by dissolving the respective metal salt of the benzoin-$P_2S_5$-reaction product of Example 1 and the succinimide in tetrahydrofuran, evaporating off the tetrahydrofuran and dissolving the soluble metal thiolate-succinimide complex in oil.

The solubilizing polyisobutenyl-succinimide dispersant component was prepared by reacting polyisobutenyl succinic anhydride wherein the number average molecular weight of the polyisobutenyl was about 950 and triethylenetetramine in a mole ratio of amine to anhydride of 0.90.

Each of the metal thiolate compounds of Example 1 listed in Table 1, prior to forming a complex with the succinimide, were essentially insoluble in oil. The metal thiolate-succinimide complexes were essentially soluble in oil.

TABLE 1

| Weight Of Compounds Of Example 1 Prepared From Benzoin, $P_2S_5$ And The Following Metals | | Weight Polyisobutylene Succinimide |
|---|---|---|
| (Mo) | 14.7 g | 85.3 g |
| (Ni) | 2.0 g | 13.6 g |
| (V) | 2.0 g | 13.6 g |
| (W) | 2.0 g | 13.6 g |
| (Cu) | 2.0 g | 13.6 g |
| (Fe) | 4.0 g | 13.6 g |
| (Co) | 2.0 g | 13.6 g |
| (Cr) | 4.0 g | 13.6 g |

Example 3

Lubricating oil compositions containing the additives of Example 2 of this invention were tested in the Oxidator B Test and the 4-Ball Weld Test.

In the Oxidator B Test, the stability of the oil is measured by the time required for the consumption of 1 liter of oxygen by 100 gm of the test oil at 340° F. In the actual test, 25 gm of oil is used and the results are corrected to 100-gm samples. The catalyst which is used at a rate of 1.38 cc per 100 cc oil contains a mixture of soluble salts providing 95 ppm copper, 80 ppm iron, 4.8 ppm manganese, 1100 ppm lead, and 49 ppm tin. The results of this test are reported as hours to consumption of 1 liter of oxygen and are a measure of the oxidative stability of the oil.

Anti-wear properties are measured by the 4-Ball Weld Test. The 4-Ball Weld Test is a variation of ASTM D-2783 run at ambient temperature until weld point with weights decreased by 5 kg until the pass load is determined.

The comparisons were made in a formulated base oil RPM 130N/480N at 85%/15% containing 30 mmoles/kg of a magnesium sulfonate, 20 mmoles/kg of a calcium phenate and 5.5% of a polymethacrylate V.I. improver.

The results of the test are shown in Table 2. The percentage of each of the metal thiolate-succinimide complexes from Example 2 are shown in Table 2.

TABLE 2

| Oxidation Inhibition Of The Succinimide Complexes | | | | |
|---|---|---|---|---|
| Metallic Thiolate-Succinimide Complexes Of Example 2 | | Oxidator B Results | | 4-Ball Weld Data |
| Metal | Wt. % | Hr./ 1 Liter | Liters/ 10 Hr. | Pass Load | Fail Load |
| (Base Oil) | 0 | 0.5 | >10 | 150 | 155 |
| Mo | 0.33 | 8.4 | 1.3 | 215 | 220 |
| Ni | 1.0 | 4.1 | 7.7 | 220 | 225 |
| V | 0.25 | 3.8 | 9.6 | — | — |
| W | 0.5 | 2.5 | 8.5 | 235 | 240 |
| Cu | 0.5 | 2.0 | 7.2 | 210 | 215 |
| Fe | 1.0 | 1.4 | 9.0 | 205 | 210 |
| Co | 0.5 | 2.1 | 9.0 | — | — |

TABLE 2-continued

| Oxidation Inhibition Of The Succinimide Complexes | | | | |
|---|---|---|---|---|
| Metallic Thiolate-Succinimide Complexes Of Example 2 | | Oxidator B Results | | 4-Ball Weld Data |
| Metal | Wt. % | Hr./ 1 Liter | Liters/ 10 Hr. | Pass Load | Fail Load |
| Cr | 1.0 | 4.5 | 5.3 | — | — |

Example 4

A formulated oil containing the molybdenum thiolate-succinimide complex of Example 2 was prepared and tested in a Sequence III-D Test method (according to ASTM Special Technical Publication 315H).

The purpose of the test is to determine the effect of the additive on the oxidation rate of the oil and the cam and lifter wear in the valve train of an internal combustion engine at relatively high temperatures (about 149° C. bulk oil temperature during testing).

In this Test, an Oldsmobile 350 CID engine was run under the following conditions:

Runs at 3,000 RPM/max. run time for 64 hours and 100 lb. load;
Air/Fuel* ratio=16.5/1, using *GMR Reference Fuel (leaded);
Timing=31° BTDC;
Oil temperature=300° F.;
Coolant temperature=in-235° F., out-245° F.;
30" of water of back pressure on exhaust;
Flow rate of jacket coolant=60 gal.min.;
Humidity must be kept at 80 grains of $H_2O$;
Air temperature controlled at the inlet equal 80° F.; and
Blowby Breather Heat Exchanger at 100° F.

The effectiveness of the additive is measured after 64 hours in terms of camshaft and lifter wear and % viscosity increase.

The comparisons were made in a formulated base oil RPM 130N/480N at 85%/15% containing 30 mmoles/kg of a magnesium sulfonate, 20 mmoles/kg of a calcium phenate, 5.5% of a polymethacrylate V.I. improver, and sufficient dialkyl zinc dithiophosphate to supply 0.05% phosphorus.

The results of the test are shown in Table 3. The amount of molybdenum thiolate-succinimide complex of Example 2 used in the oil was sufficient to provide 9 mmoles/kg of molybdenum and 3.5% of the succinimide to the formulated oil.

TABLE 3

| | Sequence III-D Test | | | |
|---|---|---|---|---|
| | Cam and Lifter Wear $\times 10^{-3}$ In. | | Viscosity | Viscosity |
| Formulation | SF Spec. Max. (8) | SF Spec. Avg. (4) | Increase % At 40 Hrs. | Increase % At 64 Hrs. |
| Base Oil | 4.4* | 2.2* | >1995 | TVTM** |
| Molybdenum Thiolate-Succinimide of Example 2 | 2.6 | 1.8 | 11 | 103 |

*Average of 2 values
**Too viscous to measure

I claim:

1. A process for preparing an oil-soluble metal thiolate-succinimide complex which comprises reacting (a) an alkyl or alkenyl mono- or bis-succinimide with (b) an oil-insoluble metal thiolate prepared by reacting (1) an acyloin of the formula:

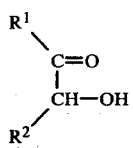

wherein $R^1$ and $R^2$ are the same or different and each is H, alkyl containing 1 to 30 carbon atoms, aryl containing 6 to 10 carbon atoms, alkaryl containing 7 to 30 carbon atoms, aralkyl containing 7 to 30 carbon atoms, or together $R^1$ and $R^2$ are alkylene and form a cyclic ring containing 4 to 6 carbon atoms which includes the carbon atoms to which they are attached, with phosphorus pentasulfide in an inert solvent at a temperature of from 25° C. to 180° C.;

wherein the mole ratio of acyloin to phosphorus pentasulfide is at least 1 to 2; and (2) reacting the product from (1) with a reactive water-soluble, ionizable compound of a heavy metal in an aqueous solution whereby the final product (b) has a thiolato ligend of the formula:

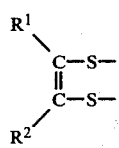

to metal ratio of from 0.5:1 to 1.5:1, and wherein the weight ratio of (a) to (b) is in the range of from 2:1 to 10:1.

2. The process of claim 1 wherein in component (a) the succinimide has the formula:

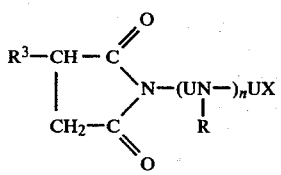

wherein X is

where R is hydrogen or alkyl of 1 to 5 carbon atoms or a group of the formula:

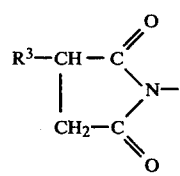

wherein $R^3$ is an alkyl or alkenyl group containing from about 20 to 300 carbon atoms; U is alkylene containing 1 to 8 carbon atoms; n is an integer of from 1 to 9; and in component (b) the acyloin has the formula:

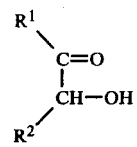

wherein $R^1$ and $R^2$ are the same or different and each is H, alkyl containing 1 to 30 carbon atoms, aryl containing 6 to 10 carbon atoms, alkaryl containing 7 to 30 carbon atoms, aralkyl containing 7 to 30 carbon atoms, or together $R^1$ and $R^2$ are alkylene and form a cyclic ring containing 4 to 6 carbon atoms which includes the carbon atoms to which they are attached; and the metal is selected from the group consisting of Co, Cr, Cu, W, Ni, Fe, V, Ti and Mo;

wherein the weight ratio of (a) to (b) is in the range of from 2:1 to 10:1.

3. The process of claim 2 wherein in component (a) the succinimide has the formula:

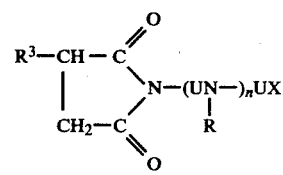

wherein U is ethylene; R is hydrogen; n is an integer of from 1 to 4; X is $NH_2$ or a group of the formula:

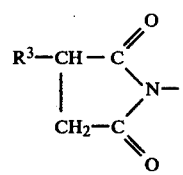

wherein $R^3$ is polyisobutylene; and
in component (b) the metal is molybdenum and the acyloin has the formula:

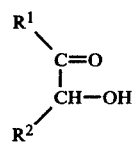

wherein $R^1$ and $R^2$ are the same or different and each is hydrogen, alkyl containing 1 to 30 carbon atoms or phenyl.

4. The process of claim 3 wherein in component (a), $R^3$ is polyisobutenyl; U is ethylene; X is $NH_2$; and n is 3 or 4; and in component (b), $R^1$ and $R^2$ are hydrogen, methyl or phenyl.

5. A lubricating oil composition comprising a major amount of an oil of lubricating viscosity and a minor proportion sufficient to inhibit oxidation and corrosion, of an oil-soluble metal thiolate-succinimide complex prepared according to the process of any one of claims 1, 2, 3, or 4.

6. A lubricating oil concentrate comprising 10% to 90% by weight of a lubricating oil and from about 90% to 10% by weight of an oil-soluble metal thiolate-succinimide complex prepared according to claim 1.

7. A composition comprising the complex prepared according to the process of any one of claims 1, 2, 3, or 4.

* * * * *

UNITED STATES PATENT AND TRADEMARK OFFICE
CERTIFICATE OF CORRECTION

PATENT NO. : 4,397,749

DATED : August 9, 1983

INVENTOR(S) : Michael A. Shippey

It is certified that error appears in the above-identified patent and that said Letters Patent are hereby corrected as shown below:

Column 2, line 56, " 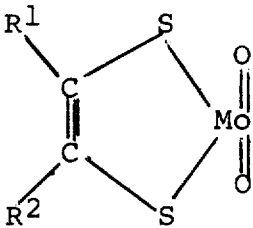 " should read

-- 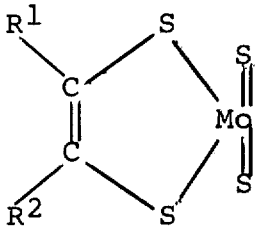 -- ....

....

Signed and Sealed this

Twenty-fifth Day of October 1983

[SEAL]

Attest:

GERALD J. MOSSINGHOFF

Attesting Officer    Commissioner of Patents and Trademarks